(12) United States Patent
Rusin et al.

(10) Patent No.: US 9,296,767 B1
(45) Date of Patent: Mar. 29, 2016

(54) SURFACE-TREATED CALCIUM PHOSPHATE PARTICLES SUITABLE FOR ORAL CARE AND DENTAL COMPOSITIONS

(71) Applicant: 3M INNOVATIVE PROPERTIES COMPANY, St. Paul, MN (US)

(72) Inventors: Richard P. Rusin, Woodbury, MN (US); Neeraj Sharma, Woodbury, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/943,170

(22) Filed: Nov. 17, 2015

Related U.S. Application Data

(62) Division of application No. 14/292,095, filed on May 30, 2014, now Pat. No. 9,220,673, which is a division of application No. 13/124,231, filed as application No. PCT/US2009/063943 on Nov. 11, 2009, now Pat. No. 8,790,707.

(60) Provisional application No. 61/121,702, filed on Dec. 11, 2008.

(51) Int. Cl.
*C07F 9/141* (2006.01)

(52) U.S. Cl.
CPC .................................. *C07F 9/1411* (2013.01)

(58) Field of Classification Search
USPC ........................................ 424/49, 57, 464, 48
See application file for complete search history.

*Primary Examiner* — Walter Webb
(74) *Attorney, Agent, or Firm* — Julie Lapos-Kuchar

(57) ABSTRACT

Calcium phosphate particles are described comprising a surface treatment wherein the surface treatment comprises at least one sugar alcohol. Also described are various oral care compositions comprising surface treated calcium phosphate particles and methods of surface treating calcium phosphate particles.

10 Claims, 1 Drawing Sheet

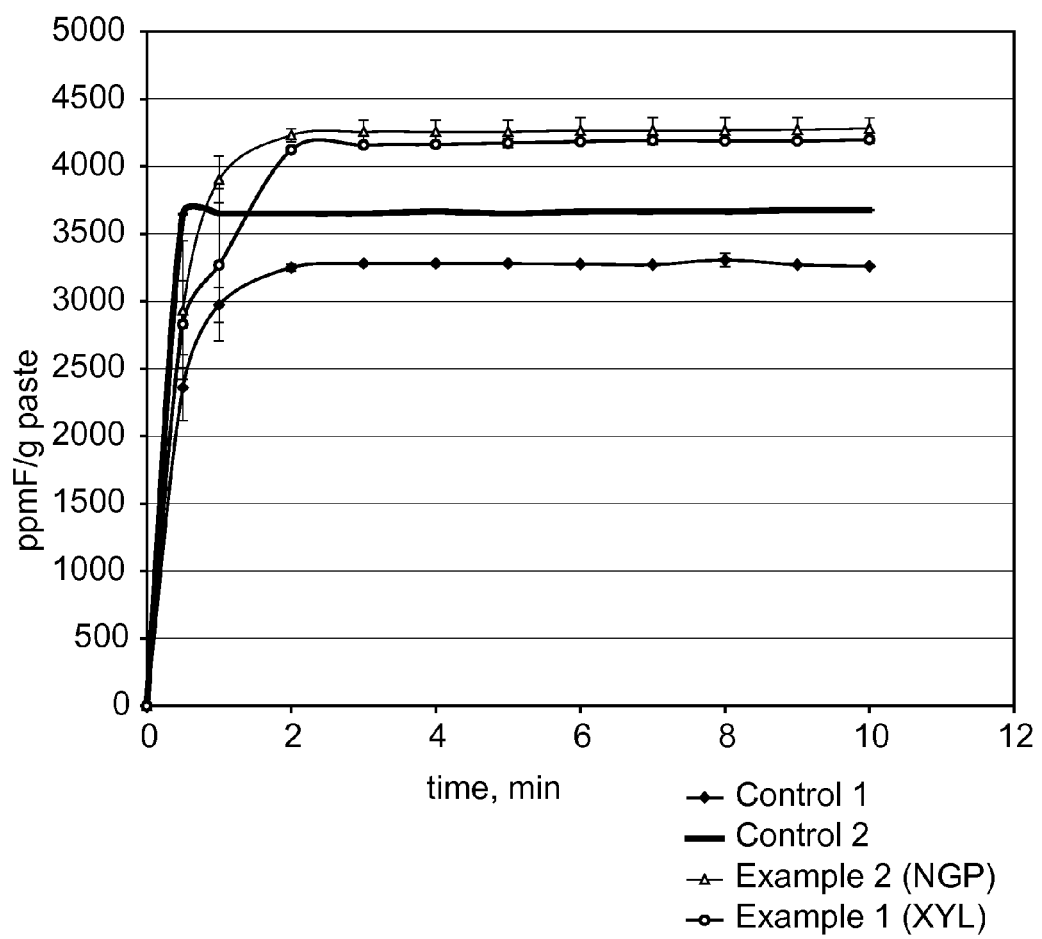

SURFACE-TREATED CALCIUM PHOSPHATE PARTICLES SUITABLE FOR ORAL CARE AND DENTAL COMPOSITIONS

CROSS REFERENCE TO RELATED APPLICATIONS

This application is a divisional of U.S. application Ser. No. 14/292,095, filed May 30, 2014, now allowed, which is a divisional of U.S. application Ser. No. 13/124,231, filed Apr. 14, 2011, now U.S. Pat. No. 8,790,707, which is a national stage filing under 35 U.S.C. 371 of PCT/US2009/063943, filed Nov. 11, 2009, which claims priority to U.S. Provisional Patent Application No. 61/121,702, filed Dec. 11, 2008, the disclosures of which are incorporated by reference in their entirety herein.

BACKGROUND

Publication No. US 2008/0187500 (abstract) describes a solid-state method of producing functionalized moieties, including placing predetermined amounts of inorganic and organic materials and milling media into a vessel rotatably connected to a turntable platform, rotating the vessel in a first direction while turning the turntable platform in a second direction counter to the first direction, milling the inorganic and organic materials into smaller respective organic and inorganic particles, and fusing portions of organic particles to inorganic parties to define functionalized moieties. The inorganic material may include calcium phosphates of varying phases, structure, and composition. The organic material may include anionic surfactants, cationic surfactants, neutral surfactants, carboxylic acids, polymers, copolymers, block copolymers, and combinations thereof.

SUMMARY

In one embodiment, tricalcium phosphate particles are described comprising a surface treatment wherein the surface treatment comprises at least one sugar alcohol, at least one glycerophosphoric acid compound, or mixture thereof.

In another embodiment, calcium phosphate particles are described comprising a surface treatment wherein the surface treatment comprises at least one sugar alcohol. The surface treated calcium phosphate particles can provide calcium and phosphorous to the (e.g. oral) environment for remineralization by neighboring teeth and bone.

In other embodiments, various oral care compositions are described comprising calcium phosphate particles surface treated with at least one sugar alcohol, at least one glycerophosphoric acid compound, or mixture thereof. Such oral care compositions preferably further comprise a fluoride-providing agent. The surface treated calcium phosphate particles are amenable to increasing the concentration of bioavailable fluoride.

In another embodiment, a method of surface treating calcium phosphate particles is also described. The method comprises dissolving at least one sugar alcohol into a liquid medium to provide a surface treatment solution; dispersing calcium phosphate particles in the surface treatment solution; and removing the liquid medium to obtain dried surface treated calcium phosphate particles.

BRIEF DESCRIPTION OF DRAWING

FIG. 1 depicts the bioavailable fluoride of embodiments of dentrifice compositions comprising surface treated calcium phosphate particles in comparison to Control 1 and Control 2.

DETAILED DESCRIPTION

Presently described are calcium phosphate particles, such as tricalcium phosphate particles, comprising a surface treatment. The surface treatment comprises at least one sugar alcohol and/or at least one glycerophosphoric acid compound.

The surface treated calcium phosphate particles are particularly useful for oral care compositions and methods for administration or application to, or use with, a human or other animal subject. As referred to herein, an "oral care composition" is any composition that is suitable for administration or application to the oral cavity of a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative, or cosmetic benefits; and combinations thereof. Typically, an oral care composition is not intentionally swallowed, but is rather retained in the oral cavity for a time sufficient to provide the intended utility. Alternatively, in some embodiments, such as when the oral care composition is for example a lozenge, soluble film, or dental varnish, the oral care composition may be ingested. Oral care compositions include, for example, dentifrices, gels, crémes, rinses, prophylactic pastes, foams, sprays, adherent strips and patches, gels, enamel conditioning materials, desensitizers, orally soluble films, tablets, chewing gums, lozenges, powders, granules, dental coatings, and dental varnishes.

Alternatively, the surface treated calcium phosphate particles can be employed in a hardenable dental composition, dental article, or orthodontic appliance.

As used herein, "dental composition" refers to an unfilled or filled (e.g. a composite) material (e.g., a dental or orthodontic material) capable of adhering (e.g., bonding) to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives such as dental fillings, liners, sealants (e.g., orthodontic sealants), and coatings. Oftentimes a dental composition can be used to bond a dental article to a tooth structure.

As used herein, "dental article" refers to an article that can be adhered (e.g., bonded) to a tooth structure. Dental articles include, for example, crowns, bridges. veneers, inlays, onlays, fillings, implants, orthodontic appliances and devices, and prostheses (e.g., partial or full dentures).

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives).

As used herein, an "oral surface" refers to a soft or hard surface in the oral environment. Hard surfaces typically include tooth structure including, for example, natural and artificial tooth surfaces, bone, tooth models, and the like.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

Calcium phosphates are inorganic compounds constituted by $Ca^{2+}$ and phosphate ions at different stoichiometric amounts that contain at least one Ca—O—P linkage. Phosphate ions are pentavalent phosphorus compounds that contain at least one phosphorus-oxygen bond. For example, the phosphate ions can be $PO_4^{3-}$, pyrophosphate $(P_2O_7^{4-})$, polyphosphate (ring and chain polyphosphates), substituted phosphates like fluorophosphates (for example, $PO_3F^{2-}$, $PO_2F_2^{-}$) and other halophosphates, thiophosphates, and amidophosphates. The calcium phosphate structure can comprise up to 50 wt-% of other ions. For example, a portion of the Ca' ions can be replaced with $Na^+$, $K^+$, $Mg^{2+}$, and mixtures thereof. Further, the oxygen atoms of the $PO_4^{3-}$ ion can be replaced with $F^-$, $CO_3^{2-}$, $OH^-$, and mixtures thereof. Typically, no greater than about 20 wt-% of other ions are present in the calcium phosphate structure. In some embodiments, the percentage of other ions in the calcium phosphate structure is no greater than 15, 10, 5, or 1 wt-%.

Suitable calcium phosphates may be any of the various crystalline or amorphous forms. Suitable calcium phosphates include tricalcium phosphate (TCP), monocalcium phosphate (MCP), dicalcium phosphate (DCP), calcium monofluorophosphate, calcium pyrophosphate (CPP), octocalcium phosphate (OCP), amorphous calcium phosphate (ACP), hydroxyapatite (HAP), fluoroapatite (FAP), tetracalcium phosphate (TTCP). Many of these have anhydrous and one or more hydrated forms. Also included are calcium phosphate materials doped with other cations or anions, e.g. Sr, Ba, Mg, Zn; Na, K, rare earths; OH, F, and carbonate. In some embodiments, the calcium phosphate is preferably tricalcium phosphate (TCP).

The calcium phosphate particles may have any finely divided form. The particles may have a wide variety of shapes, including equiaxed, spherical, oblate, discs, whiskers, fibers, platelets, etc. Generally the particle size is no greater than about 100 micrometers, and preferably no greater than about 75, 50, 25, 15, 10, 5, or even less than about 1 micron. The calcium phosphate particles may be nanoparticles, having a particle size less than 1 micron. The calcium phosphate nanoparticles may have a particle size of no greater than 500 nm, 200 nm, 150 nm, 100 nm, or even 50 nm. The particles may have a wide variety of shapes, including equiaxed, spherical, oblate, discs, whiskers, fibers, platelets, etc.

In some embodiments, the calcium phosphate particles are ground and optionally classified such that the particles are relatively monodisperse. In other embodiments, the particle may have a wide particle size distribution. For example, the largest particles may be approximately 5 to 100 times the size of the smallest particles.

The calcium phosphate particles are surface treated. There are a variety of methods for surface treating the particles. In some embodiments, the calcium phosphate particles are surface treated by means of a solution process. Solution processes typically involve dissolving or dispersing the surface treatment into a liquid (e.g. aqueous) medium; dispersing the calcium phosphate particles in the surface treatment solution; and removing the liquid to obtain dry powder. Drying may be accomplished by various means including oven drying, gap drying, spray drying, or lyophilization. Optionally, instead of drying, another liquid may be exchanged for the initial liquid medium; for example, when the liquid medium is volatile (e.g. water, ethanol), a non-volatile liquid (e.g. glycerol, methacrylate resin) may be blended into the dispersion, and then the initial liquid medium evaporated away leaving the treated particles in the new liquid, e.g. via rotary evaporation. The solution process may be aqueous, sparingly aqueous, or anhydrous. Other method of surface treating the calcium phosphate particles include milling processes, that involve comminuting or physically blending the treatment with the particulates in a mill, e.g. V-shell blender, ball mill, attritor mill, etc.; milling may be done dry or wet.

The concentration of surface treatment on the calcium phosphate particles is typically at least 0.05% by weight; in some embodiments, the concentration of surface treatment is at least 0.1, 0.2, 0.5, 1, 2, or even at least 2% by weight. The concentration of surface treatment on the calcium phosphate particles is typically no greater than about 20% by weight; in some embodiments, the concentration is no greater than about 15, 10, or even 5% by weight. In some embodiments, the concentration of surface treatment on the calcium phosphate particles ranges from about 0.1 wt-% to 10 wt-%.

In some embodiments, the surface treatment comprises at least one sugar alcohol. A sugar alcohol (also known as a polyol, polyhydric alcohol, or polyalcohol) is a hydrogenated form of carbohydrate wherein its carbonyl group (aldehyde or ketone) has been reduced to a primary or secondary alcohol. Common sugar alcohols have the general formula:

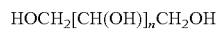

wherein n ranges from 4 to 6. In some embodiments, the sugar alcohol is preferably xylitol (n=5). In other embodiments, the sugar alcohol is erythritol (n=4) or sorbitol (n=6).

In other embodiments, the surface treatment comprises a glycerophosphoric acid compound. As used herein, glycerophosphoric acid compound refers toglycerophosphoric acid as well as salts and hydrates thereof. The glycerophosphoric acid compounds have the general formula:

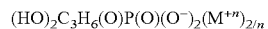

wherein M is H, or a metal ion having a valency of n.

Glycerophosphoric acid (also referred to as phosphoric acid glycerol ester exists as three isomers, beta-glycerophosphoric acid and the D(+) and L(-) forms of alpha-glycerophosphoric acid. Commercially available glycerophosphoric acid is typically a mixture of the alpha- and beta-glycerophosphoric acids.

Glycerophosphate salts may further comprise one or more waters of hydration. In preferred embodiments, the glycerophosphoric acid compound is sodium glycerophosphate, calcium glycerophosphate (CGP), or glycerophosphoric acid.

The oral care compositions described herein typically comprise an effective amount of surface treated calcium phosphate particles to enhance the natural remineralizing. The hardenable dental compositions also enhance natural remineralization, but typically at a much slower rate relative to the oral care compositions. Although the effective amount can vary, the oral care composition typically comprises at least about 0.01% calcium phosphate particles; in some embodiments, the composition may comprise at least about 0.02, 0.05, 0.08, 0.1, 0.5, 1, 2, 5, or even 8% calcium phosphate particles. The amount of calcium phosphate particles is typically no greater than 99%; in some embodiments, the amount of calcium phosphate particles is no greater than 90, 80, 70, 60, 50, or even 40%. A preferred range of calcium phosphate particles is 0.02% to 40%.

In preferred embodiments, the oral care compositions further comprise a fluoride-providing agent that is a source of fluoride-ion. Fluoride-providing agents are well known as anti-caries agents. The fluoride-providing agents are sufficiently water soluble to release an anti-carious amount of fluoride ions in water or the saliva. Suitable fluoride-providing agents are organic or inorganic.

With reference to FIG. 1, it has been found that sugar alcohols such as xylitol and glycerophosphoric acid compounds such as sodium or calcium glycerophosphate can increase the concentration of bioavailable fluoride. In some embodiments, the concentration of bioavailable fluoride of the (e.g. dentrifice) oral care composition is at least equivalent to the same (e.g. dentrifice) oral care composition lacking the surface treated calcium phosphate particles. In other embodiments, the inclusion of the surface treated calcium phosphate particles improves the concentration of bioavailable fluoride by 200 ppm/gram oral care composition, 500 ppm/gram oral care composition, or even 1,000 ppm/gram oral care composition.

Inorganic fluoride ion-providing agents include metal, alkali metal, alkaline earth metal and ammonium salts of fluoride, such as for example potassium fluoride, sodium fluoride, ammonium bifluoride, calcium fluoride, a copper fluoride such as cuprous fluoride, barium fluoride, sodium fluorosilicate, ammonium fluorosilicate, sodium fluorozirconate, sodium monofluorophosphate, aluminum mono- and di-fluorophosphate, fluorinated sodium calcium pyrophosphate, stannous fluoride, lithium fluoride, cesium fluoride, aluminum fluoride, cupric fluoride, indium fluoride, stannous fluorozirconate, ferric fluoride, nickel fluoride, palladium fluoride, silver fluoride, zirconium fluoride, and mixtures thereof. Another class of fluoride sources is fluoride-containing glasses, such as fluoroaluminosilicate glasses. Suitable fluoroaluminosilicate glasses are described in U.S. Pat. No. 5,063,257, U.S. Pat. No. 4,209,434, and U.S. Pat. No. 4,043,327. Preferred inorganic fluoride ion-providing agents are sodium monofluorophosphate, stannous fluoride, sodium fluoride, and fluoroaluminosilicate glass.

Organic fluoride ion-providing agents include hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, .delta.8-9 octadecenylbenzyldimethylammonium fluoride, dioctyldiethylammonium fluoride, cyclohexylcetyldimethylammonium fluoride, furfuryllauryidimethylammonium fluoride, phenoxyethylcetyldimethylammonium fluoride, N:N'-tetramethyl-N: N'-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyldimethylammonium fluoride, N—(B-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyidiethylammonium fluoride, N-carboxymethyl-N-cicosyldimethylammonium fluoride, olaflur (N'-octadecyltrimethylendiamine-N,N,N'-tris(2-ethanol)-dihydrofluoride), betaine hydrofluoride, sarcosine stannous fluoride, alanine stannous fluoride, glycine potassium fluoride, sarcosine potassium fluoride, glycine hydrofluoride, tetrapropylammonium tetrafluoroborate, tetrabutylammonium tetrafluoroborate, benzyltriethylammonium tetrafluoroborate, lysine hydrofluoride, alanine hydrofluoride, betaine zirconium fluoride, and mixtures thereof. Preferred organic fluoride sources include tetrapropylammonium tetrafluoroborate, tetrabutylammonium tetrafluoroborate, and benzyltriethylammonium tetrafluoroborate.

The fluoride-providing agent is present in an amount sufficient to release between about 200 ppm to 6000 ppm fluoride ion, preferably from about 800 to about 1500 ppm fluoride ion. The fluoride-providing agent may be present in the composition from about 0.001% to about 5% by weight.

The surface treated calcium phosphate particles, optionally in combination with the fluoride-providing agent, may be provided in an "orally acceptable carrier". Preferably, the carrier does not substantially reduce the efficacy of the active materials of the present compositions. Selection of specific carrier components is dependent on the desired product form, including dentifrices, rinses, gels, paints, toothpastes, tooth powders, prophylaxis pastes, as well as confectionary compositions such as lozenges, gums, and dissolvable films.

In various embodiments, the orally acceptable carrier used to prepare the oral care composition is aqueous. As recognized by one of skill in the art, the oral care compositions of the present invention optionally include other materials, such as for example, anticaries agents, including the fluoride providing agents already described, desensitizing agents, viscosity modifiers, diluents, surface active agents, such as surfactants, emulsifiers, and foam modulators, pH modifying agents, abrasives, humectants, mouth-feel agents, sweetening agents, flavor agents, colorants, preservatives, and combinations thereof.

When the surface treatment comprises a sugar alcohol, the concentration of sugar alcohol may be sufficient to concurrently sweeten the oral care composition. However, additional sugar alcohols or other sweeteners can be added as desired. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5% by weight, optionally from about 0.01% to about 1% by weight.

In preferred embodiments, the oral care composition may be a dentifrice. As referred to herein, a "dentifrice" is a composition that is intended for cleaning a hard surface within the oral cavity. Such dentifrices include toothpowder, a dental tablet, toothpaste (dental cream), or gel. In a toothpaste dentifrice, the orally acceptable vehicle may comprise water and humectant each typically in an amount ranging from about 10% to about 80% by weight of the oral care composition.

Humectants useful herein include polyhydric alcohols such as glycerin, sorbitol, xylitol and low molecular weight polyethylene glycols, including those listed above herein. In various embodiments, humectants are operable to prevent hardening of paste or gel compositions upon exposure to air. In various embodiments humectants also function as sweeteners. One or more humectants are optionally present in a total amount of about 1% to about 70% by weight, for example about 2% to about 25% by weight or about 5% to about 15% by weight.

In various embodiments, toothpastes, creams and gels contain a natural or synthetic thickener or gelling agent, which, other than silica thickeners, include natural and synthetic gums and colloids. In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly—carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

In some embodiments, the oral composition comprises substances capable of forming an adherent film or coating on the tooth or soft tissue. The duration of the coating may be minutes, hours, days, weeks, or months. Preferably, the film-forming substance is dissolved or dispersed in a liquid carrier. Preferred film-forming substances include rosins, esterified rosins, and polymeric film formers as described in provisional patent application Ser. No. 61/013,464; incorporated herein by reference. Some suitable rosins and esterified rosins are described in U.S. Pat. No. 7,335,691, US 2007/0105975, and U.S. Pat. No. 4,396,378. In various embodiments of the present invention, where the vehicle of the oral care composition is solid or a paste, the oral care composition may comprise a dentally acceptable abrasive material or polishing agent, which may serve to either polish the tooth enamel or provide a whitening effect. Any orally acceptable abrasive can be used, but type, fineness (particle size) and amount of abrasive should be selected so that tooth enamel and dentin are not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Suitable abrasive particles for oral care compositions are available from J. M Huber under the tradename ZEODENT; Grace Davison under SYLODENT; Degussa under SIDENT. Among phosphates useful as abrasives are orthophosphates, polymetaphosphates and pyrophosphates. Illustrative examples are dicalcium orthophosphate dihydrate, calcium pyrophosphate, beta-calcium pyrophosphate, tricalcium phosphate, calcium polymetaphosphate and insoluble sodium polymetaphosphate. Hence, in some embodiments, the surface treated calcium phosphate particles can serve as an abrasive concurrent with providing a source of calcium and phosphate ions. One or more abrasives are optionally present in an abrasive effective total amount, typically about 4% to about 70%, for example about 8% to about 50%, or about 10% to about 30% by weight of the composition. Average particle size of an abrasive, if present, is generally about 0.1 to about 50 μm, for example about 1 to about 40 μm or about 5 to about 30 μm.

The oral care compositions can be used in a method to treat or prevent dental caries in a human or animal subject comprising administering a safe and effective amount of an oral care composition to the oral cavity of the subject. As used herein "animal subject" includes higher order non-human mammals such as equines, canines, and felines. The oral care composition is contacted with an oral surface of the mammalian subject to thereby provide calcium and phosphate ions to promote remineralization and prevent demineralization.

The calcium phosphate particles may also be employed in a variety of hardenable dental compositions, dental articles, and orthodontic appliances, as previously described. For example, the surface treated calcium phosphate particles can be incorporated into a variety of dental and orthodontic compositions including dental varnishes and coatings; enamel lesion treatment; surface or margin-sealing gloss; adhesives and primers; desensitizing agent; dentifrice; prophy paste; restoratives; root canal filling, sealer, or primer; cements (temporary and permanent); mill blocks; gel/mousse/foam; liner/base; root and cavity desensitizing agent; pit/fissure sealant; orthodontic adhesives, cements, primers; sprays; tooth-adherent patches and strips.

The hardenable component of the dental composition can include a wide variety of chemistries, such as ethylenically unsaturated compounds (with or without acid functionality), epoxy (oxirane) resins, vinyl ethers, (e.g. photopolymerization) initiator systems, redox cure systems, glass ionomer cements, polyethers, polysiloxanes, and the like.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions of the present invention include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

The (e.g., photopolymerizable) dental compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis [1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth) acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in PCT International Publication Nos. WO 00/38619 (Guggenberger et al.), WO 01/92271 (Weinmann et al.), WO 01/07444 (Guggenberger et al.), and WO 00/42092 (Guggenberger et al.); and fluoropolymer-functional (meth)acrylates as disclosed, for example, in U.S. Pat. No. 5,076,844 (Fock et al.) and U.S. Pat. No. 4,356,296 (Griffith et al.) and European Pat. Application Publication Nos. EP 0373 384 (Wagenknecht et al.), EP 0201 031 (Reiners et al.), and EP 0201 778 (Reiners et al.). Mixtures of two or more free radically polymerizable compounds can be used if desired.

The hardenable dental composition may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

| Abbreviations, Descriptions, and Sources of Materials | |
|---|---|
| Abbreviation | Description and Source of Material (Unless otherwise indicated, available from Sigma-Aldrich, St. Louis, MO.) |
| TCP | Tricalcium phosphate (Fluka) |
| Xyl | Xylitol (Spectrum Chemical Manufacturing) |
| NGP | Sodium glycerophosphate (Kodak) |

Example 1

Surface Treatment of TCP with 2% Xylitol 31.9 g of TCP was blended with 1.3 g of a 60% aqueous solution of xylitol and 36.1 g of deionized water (DIW) to form a thin slurry; stirred for 1 hr; dried at 80 C for 18 hr. The resulting soft cake crushed readily to yield fine powder, and was calculated to have 2% xylitol treatment on the TCP powder.

Example 2

Surface Treatment of TCP with 2% NGP 33.6 g of TCP was blended with 2.2 g of a 34.1% aqueous solution of NGP and 52.9 g of DIW to form a thin slurry; stirred for 1 hr; dried at 80 C for 18 hr. The resulting soft cake crushed readily to yield fine powder, and was calculated to have 2% NGP treatment on the TCP powder.

Examples 3 and 4

Dentifrice Formulations

Two dentifrice formulations were compounded by mixing 0.5% of the surface treated TCP with 99.5% of a toothpaste commercially available from 3M ESPE, under the trade designation "Omni ControlRx Prescription Fluoride Toothpaste". The ingredients listed on the product label include 1.1% neutral sodium fluoride (5000 ppm F)(w/w), MICRODENT™, deionized water, sorbitol, hydrated silica, glycerin, PEG-12, cellulose gum, sodium lauryl sulfate, flavor, titanium dioxide, and sodium saccharin.

Bioavailable Fluoride Test 2 g of the paste or solution are injected via syringe into 40 g of a 1:1 solution of Total Ionic Strength Adjustment Buffer (Thermo Orion, Beverly, Mass.) and deionized water (paste: solution=1:20). Fluoride is measured via a fluoride-selective electrode before adding paste (t=0); then 30 sec; 1 min; and each minute after for 10 min total.

Data collected for modified ControlRx formulations are shown in FIG. 1, along with unmodified ControlRx toothpaste (Control 1) and an aqueous sodium fluoride (5000 ppm F) solution (Control 2) for comparison.

Hardenable Dental Compositions

3M™ ESPE™ Vitrebond™ Plus Light Cure Glass Ionomer Liner/Base

3M™ ESPE™ Clinpro™ Sealant

Omni™ Vanish™ 5% Sodium Fluoride White Varnish (3M™ ESPE™)

| | Hardenable Composition | Surface Treated Particles | % Treated Particles in composition |
|---|---|---|---|
| Example 5 | 12.6 g white glass-containing paste component of Vitrebond Plus liner/base | 0.41 g of surface treated particles of Example 2 (2 wt-% NGP) | 3.2 wt % |
| Example 6 | 12.6 g white glass-containing paste component of Vitrebond Plus liner/base | 0.38 g of surface treated particles of Example 1 (2 wt-% xylitol) | 3.0 wt % |
| Example 7 | 3.2 g Clinpro sealant | 0.15 g of surface treated particles of Example 2 (2 wt-% NGP) | 4.5 wt % |
| Example 8 | 3.2 g Clinpro sealant | 0.18 g of surface treated particles of Example 1 (2 wt-% xylitol) | 5.3 wt % |

-continued

| | Hardenable Composition | Surface Treated Particles | % Treated Particles in composition |
|---|---|---|---|
| Example 9 | 2.7 g Vanish varnish | 0.16 g of surface treated particles of Example 2 (2 wt-% NGP) | 5.6 wt % |

The compositions in the table were mixed into smooth, creamy pastes. The following evaluations were conducted:

Examples 5-6

A small, pea-sized amount of each paste was mixed with an equivalent volume of the clear liquid component of Vitrebond Plus liner/base. The mixing and handling was the same as that of Vitrebond Plus liner/base. A portion of the mixed material was illuminated with light from a calibrated 3M™ ESPE™ Freelight™ 2 Dental Curing Light for 20 sec, resulting in a hard, polymerized material. These pastes are suitable for use as a component of a dental liner/base.

Examples 7-8

The handling of this paste was examined using a mixing stick and a dental fiber tip applicator. This paste exhibited the same handling properties as Clinpro sealant. A portion of the paste was illuminated with light from a calibrated 3M™ ESPE™ Freelight™ 2 Dental Curing Light for 20 sec, resulting in a hard, polymerized material. These compositions are suitable for use as a dental sealant.

Example 9

The composition was painted onto a frosted glass slide in a thin layer using the brush provided with the Vanish varnish product. This paste exhibited the same creamy, easy-to-spread handling properties as Vanish varnish. After approximately 10 min in air the layer dried to form a soft film, the same as that formed by Vanish varnish under similar conditions. This composition is suitable for use as a dental varnish.

What is claimed is:

1. A method of surface treating calcium phosphate particles comprising
   dissolving at least one sugar alcohol into a liquid medium to provide a surface treatment solution;
   dispersing calcium phosphate particles in the surface treatment solution; and
   removing the liquid medium to obtain dried surface treated calcium phosphate particles.

2. The method of claim 1 wherein the liquid medium is an aqueous medium.

3. The method of claim 1, wherein the calcium phosphate particles comprise tricalcium phosphate.

4. The method of claim 1, wherein the sugar alcohol has the general formula $HOCH_2[CH(OH)]_nCH_2OH$, wherein n ranges from 4 to 6.

5. The method of claim 4, wherein the sugar alcohol is xylitol.

6. The method of claim 1, wherein the calcium phosphate particles comprise at least one of: Sr, Ba, Mg, Zn; Na, K, a rare earth metal, OH, F, carbonate, and combinations thereof.

7. The method of claim 1, wherein the calcium phosphate particles have a particle size no greater than 100 micrometers.

8. The method of claim 1, wherein the calcium phosphate particles have a particle size no greater than 500 nanometers.

9. The method of claim 1, wherein the largest calcium phosphate particles are 5 to 100 times the size of the smallest calcium phosphate particles.

10. The method of claim 1, wherein the concentration of surface treatment on the calcium phosphate particles is at least 0.05% by weight.

* * * * *